(12) United States Patent
Koltz, Jr. et al.

(10) Patent No.: US 12,397,123 B2
(45) Date of Patent: Aug. 26, 2025

(54) SURGICAL GAS DELIVERY SYSTEM AND METHOD FOR GAS SEALED INSUFFLATION AND RECIRCULATION WITH UVC STERILIZATION

(71) Applicant: Conmed Corporation, Utica, NY (US)

(72) Inventors: Michael Koltz, Jr., Aurora, CO (US); Jonathan Teymouri, Aurora, CO (US)

(73) Assignee: Conmed Corporation, Largo, FL (US)

( * ) Notice: Subject to any disclaimer, the term of this patent is extended or adjusted under 35 U.S.C. 154(b) by 892 days.

(21) Appl. No.: 17/155,478

(22) Filed: Jan. 22, 2021

(65) Prior Publication Data
US 2022/0233790 A1 Jul. 28, 2022

(51) Int. Cl.
- *A61M 13/00* (2006.01)
- *A61B 17/34* (2006.01)
- *A61L 9/20* (2006.01)

(52) U.S. Cl.
CPC ....... *A61M 13/006* (2014.02); *A61B 17/3423* (2013.01); *A61L 9/20* (2013.01); *A61M 2205/3606* (2013.01)

(58) Field of Classification Search
CPC ................ A61M 13/00; A61M 13/003; A61M 13/006; A61M 2205/053; A61M 2205/3606; A61M 2205/362; A61M 2202/203; A61M 2202/206; A61L 9/20; A61L 2209/12; A61B 17/3423; A61B 17/3462

See application file for complete search history.

(56) References Cited

U.S. PATENT DOCUMENTS

| | | | | |
|---|---|---|---|---|
| 5,006,109 | A * | 4/1991 | Douglas | A61M 13/003 600/560 |
| 6,220,245 | B1 * | 4/2001 | Takabayashi | A61M 16/0057 128/202.13 |
| 7,854,724 | B2 | 12/2010 | Stearns et al. | |
| 8,795,223 | B2 | 8/2014 | Stearns et al. | |
| 9,199,047 | B2 | 12/2015 | Stearns et al. | |
| 9,375,539 | B2 | 6/2016 | Stearns et al. | |
| 10,702,306 | B2 | 7/2020 | Silver et al. | |
| 2006/0254590 | A1 * | 11/2006 | Berry | A61M 16/0093 128/205.12 |
| 2008/0161749 | A1 * | 7/2008 | Houghton-Ward | A61M 35/30 604/23 |
| 2011/0060272 | A1 | 3/2011 | Iranitalab | |

(Continued)

FOREIGN PATENT DOCUMENTS

CN 212326475 U 1/2021

OTHER PUBLICATIONS

Extended European Search Report dated Dec. 13, 2024, issued during the prosecution of EP 22743056.8.

*Primary Examiner* — Kami A Bosworth
*Assistant Examiner* — Avery Smale
(74) *Attorney, Agent, or Firm* — Troutman Pepper Locke LLP; Scott D. Wofsy

(57) ABSTRACT

A surgical gas delivery system is disclosed for gas sealed insufflation and recirculation during an endoscopic or laparoscopic surgical procedure, which includes a gaseous sealing manifold for communicating with a gas sealed access port, a compressor for recirculating gas through the gaseous sealing manifold, and a source of UVC irradiation for sterilizing at least the gas recirculating through the gaseous sealing manifold.

7 Claims, 1 Drawing Sheet

(56) References Cited

U.S. PATENT DOCUMENTS

2014/0309583 A1   10/2014  Stearns et al.
2015/0202389 A1*  7/2015  Stearns .............. A61B 17/3421
                                                          604/23
2017/0119940 A1*  5/2017  Quisenberry ......... A61M 1/964

* cited by examiner

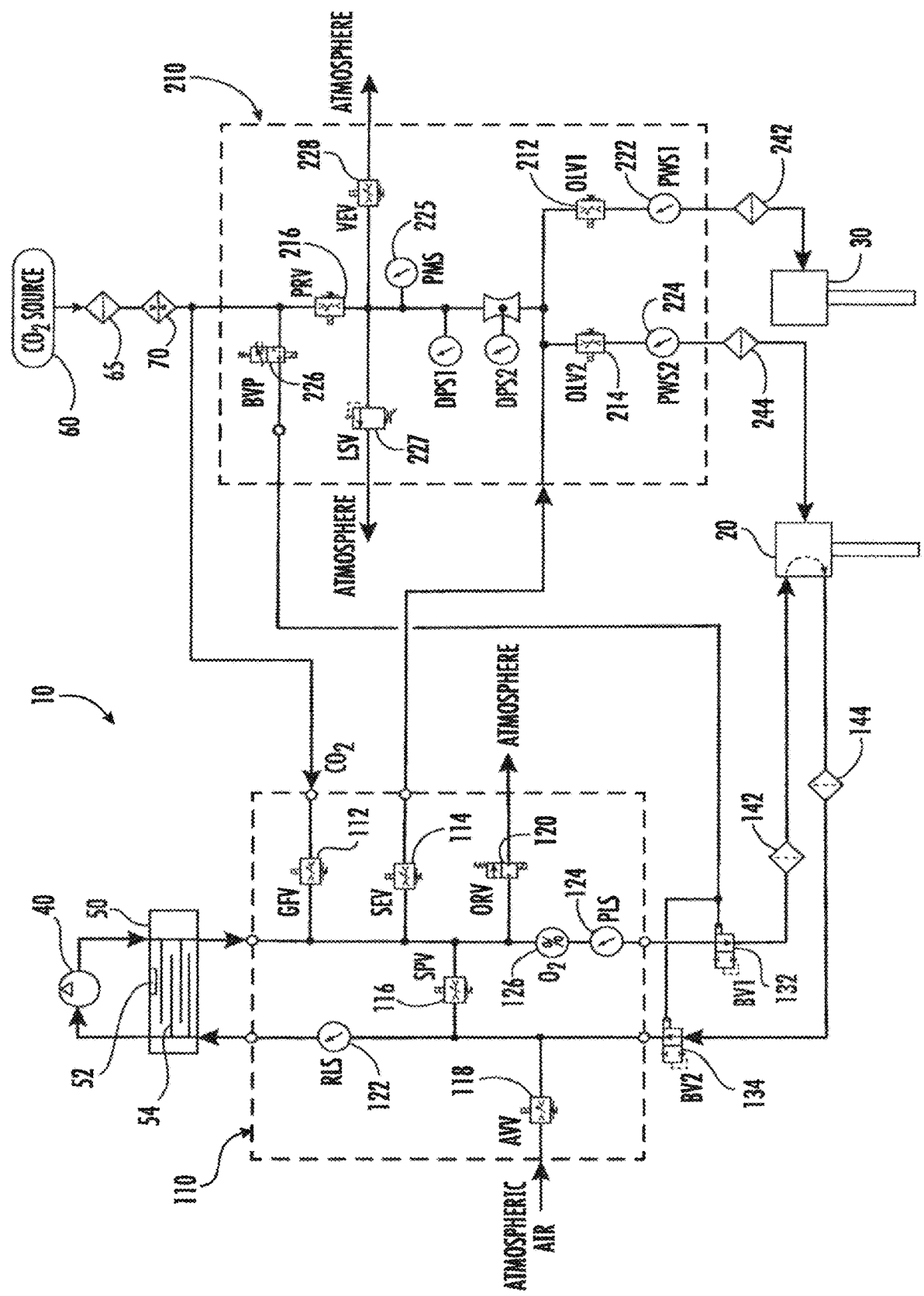

SURGICAL GAS DELIVERY SYSTEM AND METHOD FOR GAS SEALED INSUFFLATION AND RECIRCULATION WITH UVC STERILIZATION

BACKGROUND OF THE INVENTION

1. Field of the Invention

The subject invention is directed to minimally invasive surgery, and more particularly, to a surgical gas delivery system and method for gas sealed insufflation and recirculation with internal UVC gas sterilization for use during an endoscopic or laparoscopic surgical procedure.

2. Description of Related Art

Laparoscopic or "minimally invasive" surgical techniques are becoming commonplace in the performance of procedures such as cholecystectomies, appendectomies, hernia repair and nephrectomies. Benefits of such procedures include reduced trauma to the patient, reduced opportunity for infection, and decreased recovery time. Such procedures within the abdominal (peritoneal) cavity are typically performed through a device known as a trocar or cannula, which facilitates the introduction of laparoscopic instruments into the abdominal cavity of a patient.

Additionally, such procedures commonly involve filling or "insufflating" the abdominal cavity with a pressurized fluid, such as carbon dioxide, to create an operating space, which is referred to as a pneumoperitoneum. The insufflation can be carried out by a surgical access device, such as a trocar, equipped to deliver insufflation fluid, or by a separate insufflation device, such as an insufflation (veress) needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the surgical access devices themselves, often using a separate inserter or obturator placed therein. Following insertion, the obturator is removed, and the trocar allows access for instruments to be inserted into the abdominal cavity. Typical trocars provide a pathway to insufflate the abdominal cavity, so that the surgeon has an open interior space in which to work.

The trocar must also provide a way to maintain the pressure within the cavity by sealing between the trocar and the surgical instrument being used, while still allowing at least a minimum amount of freedom of movement for the surgical instruments. Such instruments can include, for example, scissors, grasping instruments, and occluding instruments, cauterizing units, cameras, light sources and other surgical instruments. Sealing elements or mechanisms are typically provided on trocars to prevent the escape of insufflation gas from the abdominal cavity. These sealing mechanisms often comprise a duckbill-type valve made of a relatively pliable material, to seal around an outer surface of surgical instruments passing through the trocar.

SurgiQuest, Inc., a wholly owned subsidiary of ConMed Corporation has developed unique gas sealed surgical access devices that permit ready access to an insufflated surgical cavity without the need for conventional mechanical valve seals, as described, for example, in U.S. Pat. Nos. 7,854,724 and 8,795,223. These access devices are constructed from several nested components including an inner tubular body portion and a coaxial outer tubular body portion. The inner tubular body portion defines a gas sealed central lumen for introducing conventional laparoscopic or endoscopic surgical instruments to the surgical cavity of a patient and the outer tubular body portion defines an annular lumen surrounding the inner tubular body portion for delivering insufflation gas to the surgical cavity of the patient and for facilitating periodic sensing of abdominal pressure.

SurgiQuest has also developed multimodal surgical gas delivery systems for use with the unique gas sealed access devices described above. These gas delivery systems, which are disclosed for example in U.S. Pat. Nos. 9,199,047 and 9,375,539 have a first mode of operation for providing gas sealed access to a body cavity, a second mode of operation for performing smoke evacuation from the body cavity, and a third mode of operation for providing insufflation gas to the body cavity.

The efficacy of Ultraviolet light to reduce nosocomial infections in operating rooms, patient rooms and chronic care facilities caused by bacterial, viral and fungal microorganisms is well documented. The reduction of viral loads in blood, serum and other body fluids by way of Ultraviolet light application has also been demonstrated. Studies have also documented reduction of bacterial colonies in open wounds and burn victims using UV light treatment.

To date however, the use of UV light to reduce viral and/or bacterial microorganisms that may be carried by surgical gases delivered to and from a surgical cavity during a laparoscopic or endoscopic surgical procedure has not been demonstrated. It would be beneficial therefore to employ UV light in a surgical gas delivery system to sterilize the gas flow and reduce or otherwise eliminate viral and/or bacterial loads carried in the surgical gases, as well as to sterilize the gas flow passages of the gas delivery device itself.

SUMMARY OF THE DISCLOSURE

A new and useful surgical gas delivery system is disclosed for gas sealed insufflation and recirculation during an endoscopic or laparoscopic surgical procedure, which includes a gaseous sealing manifold for communicating with a gas sealed access port, a compressor for recirculating gas through the gaseous sealing manifold, and a source of UVC irradiation for sterilizing at least the gas recirculating through the gaseous sealing manifold.

Preferably, the system further includes an intercooler or condenser that is interposed between the compressor and the gaseous sealing manifold for conditioning gas flowing therethrough. The source of UVC irradiation is positioned within the intercooler or condenser to sterilize internal flow passages thereof and the gas flowing therethrough. The source of UVC irradiation includes at least one light source that is in communication with the internal flow passages of the intercooler or condenser, and which is adapted and configured to generate UVC radiation at a wavelength of about between 240-350 nm. The light source can be either an LED light source or a florescent light source.

The subject invention is also directed to a method of surgical gas delivery during a surgical procedure which includes the steps of recirculating gas through a gas sealed access port to provide gas sealed access to a body cavity and to maintain a stable cavity pressure during the surgical procedure, and sterilizing the gas recirculating through the gas sealed access port by way of UVC irradiation at a wavelength of about between 240-350 nm, wherein the gas recirculating through the gas sealed access port is preferably sterilized at a wavelength of about 265 nm.

These and other features of the gas delivery system and method of the subject invention will become more readily apparent to those having ordinary skill in the art to which the subject invention appertains from the detailed description of the preferred embodiments taken in conjunction with the following brief description of the drawings.

BRIEF DESCRIPTION OF THE DRAWINGS

So that those skilled in the art will readily understand how to make and use the gas delivery system and method of the subject invention without undue experimentation, preferred embodiments thereof will be described in detail herein below with reference to the FIGURES wherein:

FIG. 1 is a schematic diagram of the multi-modal gas delivery system of the subject invention, which includes a gaseous sealing manifold for communicating with a gas sealed access port and an insufflation manifold for communicating with the gas sealed access port and with a valve sealed access port, wherein the gas delivery system includes a condenser or intercooler that has an internal source of UVC irradiation for sterilizing internal flow passages thereof and the gas flowing therethrough.

DETAILED DESCRIPTION OF THE PREFERRED EMBODIMENTS

Referring now to the drawings wherein like reference numerals identify similar structural elements and features of the subject invention, there is illustrated in FIG. 1 a new and useful multi-modal surgical gas delivery system 10 that is adapted and configured for gas sealed insufflation, recirculation and smoke evacuation during an endoscopic or laparoscopic surgical procedure. The multi-modal surgical gas delivery system 10 of the subject invention includes a gaseous sealing manifold 110 for communicating with a gas sealed access port 20 and an insufflation manifold 210 for communicating with the gas sealed access port 20 and with a valve sealed access port 30.

The gas sealed access port 20 is of the type disclosed in commonly assigned U.S. Pat. No. 8,795,223, which is incorporated herein by reference. The gas sealed access port 20 is adapted and configured to provide gas sealed instrument access to a body cavity, while maintaining a stable pressure within the body cavity (e.g., a stable pneumoperitoneum in the peritoneal or abdominal cavity). In contrast, the valve sealed access port 30 is a conventional or standard trocar, for providing access to a body cavity through a mechanical valve seal, such as, for example, a duckbill seal, septum seal or the like. Depending upon the requirements of a particular surgical procedure, the multi-modal gas delivery system 10 can be utilized with either the gas sealed access port 20, the valve sealed access port 30 or with both access ports 20, 30 at the same time.

The gas delivery system 10 further includes a compressor or positive pressure pump 40 for recirculating surgical gas through the gas sealed access port 20 by way of the gaseous sealing manifold 110. The compressor 40 is preferably driven by a brushless DC (direct-current) motor, which can be advantageously controlled to adjust gas pressure and flow rates within the gas delivery system 10, as disclosed for example in commonly assigned U.S. Pat. No. 10,702,306, which is incorporated herein by reference. Alternatively, the compressor 40 can be driven by an AC motor, but a DC motor will be relatively smaller and lighter, and therefore more advantageous from a manufacturing standpoint.

An intercooler and/or condenser 50 is operatively associated with the compressor 40 for cooling or otherwise conditioning gas recirculating through the gaseous sealing manifold 110. A UVC irradiator 52 is operatively associated with the intercooler or condenser 50 for sterilizing gas recirculating through the internal flow passages 54 formed therein by way of the compressor 40. In addition, the UVC irradiator is intended to sterilize the interior surfaces of the gas conduits or flow passages through which the gas flows within the intercooler/condenser 50.

The UVC irradiator 52 preferably includes at least one LED light source or a florescent light source that is adapted and configured to generate UVC radiation at a wavelength of about between 240-350 nm, and preferably about 265 nm. This ultraviolet light at such a wavelength can sterilize viral, bacterial and microbial bodies within the gas conduits of the system, and can reduce coronavirus including SARS-COV-2.

Preferably, compressor 40, intercooler/condenser 50, gaseous sealing manifold 110 and insufflation manifold 210 are all enclosed within a common housing, which includes a graphical user interface and control electronics, as disclosed for example in commonly assigned U.S. Pat. No. 9,199,047, which is incorporated herein by reference.

The gas delivery system 10 further includes a surgical gas source 60 that communicates with the gaseous sealing manifold 110 and the insufflation manifold 210. The gas source 60 can be a local pressure vessel or a remote supply tank associated with a hospital or healthcare facility. Preferably, gas from the surgical gas source 60 flows through a high pressure regulator 65 and a gas heater 70 before it is delivered to the gaseous sealing manifold 110 and the insufflation manifold 210. Preferably, the high pressure regulator 65 and the gas heater 70 are also enclosed with the compressor 40, intercooler 50, gaseous sealing manifold 110 and insufflation manifold 210 in the common housing.

The gas delivery system 10 further includes a first outlet line valve (OLV1) 212 that is operatively associated with the insufflation manifold 210 for controlling a flow of insufflation gas to the valve sealed access port 30 and a second outlet line valve (OLV2) 214 that is operatively associated with the insufflation manifold 210 for controlling a flow of insufflation gas to the gas sealed access port 20.

In accordance with a preferred embodiment of the subject invention, the first and second outlet line valves 212, 214 of insufflation manifold 210 are proportional valves that are configured to dynamically alter or otherwise control the outflow of insufflation gas to the access ports 20, 30 to match volume fluctuations that may arise in a patient's body cavity as they occur. The first and second proportional outlet line valves 212, 214 provide the gas delivery system 10 with fine control of insufflation gas flow rate to achieve stable flow rates at lower pressure, reduce pressure oscillation and eliminate pneumatic hammer.

Because the first and second proportional outlet line valves 212, 214 are proximal to the patient where flow friction losses are relatively low, the gas delivery system 10 is able to measure peritoneal pressures accurately. Moreover, the use of proportional outlet line valves for this purpose is uniquely possible here, because there is constant gas recirculation throughout the gas delivery system 10, either by way of closed loop smoke evacuation or by way of the gas sealed access port 20.

Proportional valves allow for infinitely variable gas flow adjustment between a minimum flow state and a maximum flow state. Given that some volume changes in a patient's body cavity, such as breathing, are expected and consistent, by employing proportional outlet line valves, the insufflation manifold 210 is able to dynamically alter the gas flow to the body cavity to inverse the expected volume changes, resulting in a neutral effect on the pressure inside the cavity.

An additional benefit of using proportional valves for controlling the outflow of insufflation gas from manifold 210 is a reduction in response time, as compared to that of a solenoid valve. A solenoid valve operates by applying energy to coils, which produces an electromagnetic force that moves a piston. However, the energizing of the coils takes some amount of time, introducing a delay between a commanded action and the physical movement of the piston. In contrast, proportional valves, as employed in the gas delivery system 10 of the subject invention, do not have an energization delay in general, and so they have an improved response time as compared to solenoid valves.

The insufflation manifold 210 further includes a first patient pressure sensor (PWS1) 222 downstream from the first outlet line valve 212 and a second patient pressure sensor (PWS1) 224 downstream from the second outlet line valve 214. These two patient pressure sensors are used to measure abdominal pressure to control outlet line valves 212, 214, respectively. Two other pressure sensors are located upstream from the outlet line valves 212, 214, and are labeled as DPS1 and DPS2. These two pressure sensors are situated within a venturi to measure a pressure differential that is used to infer a total gas flow rate from the insufflation manifold 210 to the patient's body cavity.

A primary proportional valve (PRV) 216 is also operatively associated with insufflation manifold 210 and it is located upstream from the first and second outlet line valves 212, 214 to control the flow of insufflation gas to the first and second outlet line valves 212, 214. Proportional valve 216 functions to maintain an intermediate pressure within the insufflation manifold 210 (as the central node in the LPU) at a constant pressure between 1 and 80 mmHg, dependent on the system operating mode. The opening of PRV 216 can be indirectly initiated by any of the following actions: patient respiration, gas leakage downstream of PRV 216, or the opening of the safety valve LSV 227 or ventilation valve VEV 228, i.e. any event that causes an intermediate pressure to drop. In the system. LSV 227 and VEV 228 are described in more detail below.

The gaseous sealing manifold 110 also includes a high pressure gas fill valve (GFV) 112 that is operatively associated with an outlet side of the compressor 40. GFV 112 is adapted and configured to control gas delivered into the gaseous sealing manifold 110 from the source of surgical gas 60. Preferably, the gas fill valve 112 is a proportional valve that is able to dynamically control surgical gas delivered into the gaseous sealing manifold 110.

The gaseous sealing manifold 110 also includes a smoke evacuation valve (SEV) 114 that is operatively associated with an outlet side of the compressor 40 for dynamically controlling gas flow between the gaseous sealing manifold 110 and the insufflation manifold 210 under certain operating conditions, such as, for example, when the gas delivery device 10 is operating in a smoke evacuation mode. Preferably, the smoke evacuation valve 114 is a proportional valve.

A bypass valve (SPV) 116 is positioned between an outlet side of the compressor 40 and an inlet side of the compressor 40 for controlling gas flow within the gaseous sealing manifold 110 under certain operating conditions. Preferably, the bypass valve 116 is a proportional valve, which is variably opened to establish and control the gaseous seal generated within gas sealed access port 20. Moreover, bypass valve 116 controls gas flow rate to the gaseous seal using feedback from pressure sensors 122, 124, described in further detail below.

The gaseous sealing manifold 110 also includes an air ventilation valve (AVV) 118, which is operatively associated with an inlet side of the compressor 40 for controlling the entrainment of atmospheric air into the system 10 under certain operating conditions. For example, AVV 118 will permit the introduction of atmospheric air into the gaseous sealing circuit to increase the air mass (i.e., the standard volume) within the circuit. The thermodynamics of clinical use conditions can cause a loss of standard volume within the gas circuit. The ventilation valve 118 permits the gas delivery system 10 to make up for this lost volume, in order to ensure that pump pressure and flow rates are sufficient to maintain the gaseous seal within the gas sealed access port 20. The ventilation valve 118 can also be opened to reduce the vacuum side pressure in the gas seal circuit.

An overpressure relief valve (ORV) 120 is operatively associated with an outlet side of the compressor 40 for controlling a release of gas from the system 10 to atmosphere under certain operating conditions. Preferably, the overpressure relief valve 120 is a proportional valve that is opened to reduce the positively pressurized side of the gas seal circuit, especially in the event of an emergency, such as a loss of power to the gas delivery system 10. The normally open configuration of relief valve 120 reduces the risk of over-pressurization of the patient cavity upon loss of power to that valve.

A first pressure sensor (RLS) 122 is operatively associated with an inlet side of the compressor 40 and a second pressure sensor (PLS) 124 is operatively associated with an outlet side of the compressor 40. These pressure sensors 122, 124 are situated to have unobstructed and minimally restricted commutation with the patient's abdominal cavity in order to continuously and accurately measure cavity pressure. The signals from these two pressure sensors 122, 124 are employed by a controller of the gas delivery system 10 to modulate the opening of the two outlet line valves 212 and 214, to control the patient cavity pressure.

In addition, the gaseous sealing manifold 110 includes a gas quality sensor 126 that is operatively associated with an outlet side of the compressor 40. The gas quality sensor monitors the level of oxygen in the recirculation circuit, which corresponds to a concentration of $CO_2$ in the body cavity of a patient, as disclosed in U.S. Pat. No. 9,199,047.

A first blocking valve (BV1) 132 is operatively associated with an outlet flow path of the gaseous sealing manifold 110 and a second blocking valve (BV2) 134 is operatively associated with an inlet flow path to the gaseous sealing manifold 110. The blocking valves 132, 134 are employed during a self-test prior to a surgical procedure, as disclosed in U.S. Pat. No. 9,199,047. It is envisioned that the first and second blocking valves 132, 134 could be are mechanically actuated or pneumatically actuated.

A first filter element 142 is positioned downstream from the first blocking valve 132 for filtering pressurized gas flowing from the compressor 40 to the gas sealed access port 20, and a second filter element 144 is positioned upstream from the second first blocking valve 134 for filtering gas returning to the compressor 40 from the gas sealed access port 20. Preferably, the filter elements 142, 144 are housed within a common filter cartridge, as disclosed for example in U.S. Pat. No. 9,199,047.

The first and second blocking valves 132, 134 communicate with a blocking valve pilot (BVP) 226 that is included within with the insufflation manifold 210. Preferably, the blocking valve pilot 226 is a solenoid valve. It is envisioned that BVP 226 could be fed from the compressor outlet as shown or from a gas source such of surgical gas or air. The insufflation manifold 110 further includes a pressure sensor (PMS) 225 located downstream from the primary proportional valve 216 and upstream from the outlet line valves 212, 214. The two outlet line valves are opened to introduce insufflation gas to the patient's body cavity by way of the access ports 23, 30. This introduction of gas has the effect of increasing pressure within the body cavity. Additionally, the outlet line valves 212, 214 can be opened in conjunction with air ventilation valve 228 to release gas from the body cavity, having the effect of desufflation and reduction of cavity pressure.

The insufflation manifold 210 further includes a low pressure safety valve (LSV) 227 downstream from the primary proportional valve 216 and upstream from the first and second outlet line valves 212, 214 for controlling a release of gas from the system 10 to atmosphere under certain operating conditions. LSV 227 is a purely mechanical valve that functions to limit the maximum intermediate pressure within the manifold 210 or LPU (Low Pressure Unit) in the event of a power interruption, a pressure controller malfunction or if a valve located upstream from the LSV sticks in an open position.

In addition, a ventilation exhaust valve (VEV) 228 is positioned downstream from the primary proportional valve 216 and upstream from the outlet line valves 212, 214 for controlling a release of gas from the system 10 to atmosphere under certain operating conditions. The ventilation exhaust valve 228 is a preferably a proportional valve that is opened to desufflate or otherwise reduce patient cavity pressure. Additionally, VEV 228 can be opened to reduce intermediate pressure within the LPU.

A filter element 242 is positioned downstream from the first outlet line valve 212 for filtering insufflation gas flowing from the insufflation manifold 210 to the valve sealed access port 30. Another filter element 244 is positioned downstream from the second outlet line valve 224 for filtering insulation gas flowing from the insufflation manifold 210 to the gas sealed access port 20. Preferably, filter element 244 is housed with filter elements 142 and 144 in a common filter cartridge, while filter element 242 is separately located.

While the gas delivery system of the subject disclosure has been shown and described with reference to preferred embodiments, those skilled in the art will readily appreciate that changes and/or modifications may be made thereto without departing from the scope of the subject disclosure.

What is claimed is:

1. A surgical gas delivery system for gas sealed insufflation and recirculation comprising:
   a) a gaseous sealing manifold for communicating with a gas sealed access port;
   b) a compressor for recirculating gas through the gaseous sealing manifold;
   c) an intercooler or a condenser interposed between the compressor and the gaseous sealing manifold for conditioning the gas recirculating through the intercooler or the condenser, wherein the gas recirculating through the intercooler or the condenser passes through the intercooler or the condenser twice, once before entering the compressor and then again after exiting the compressor, wherein:
      the gas flows directly from an outlet of the gaseous sealing module to a first inlet of the intercooler or the condenser, and then directly from a first outlet of the intercooler or the condenser to an inlet of the compressor during a first pass through the intercooler or the condenser, and
      the gas then flows directly from an outlet of the compressor to a second inlet of the intercooler or the condenser, and then directly from a second outlet of the intercooler or the condenser to an inlet of the gaseous sealing module during a second pass through the intercooler or the condenser; and
   d) a source of UV irradiation located within the intercooler or the condenser for sterilizing the gas recirculating through the intercooler or the condenser during the first pass and during the second pass.

2. The system recited in claim 1, wherein the source of UV irradiation includes at least one light source that is adapted and configured to generate UV radiation at a wavelength of about between 240-350 nm.

3. The system recited in claim 2, wherein the at least one light source is an LED light source or a florescent light source.

4. The system recited in claim 1, wherein a source of surgical gas communicates with the gaseous sealing manifold.

5. The system recited in claim 4, further comprising an insufflation manifold for communicating with the gas sealed access port, and wherein the insufflation manifold communicates with the source of surgical gas.

6. The system recited in claim 5, wherein the insufflation manifold is adapted and configured to communicate with the gas sealed access port and with a valve sealed access port.

7. The system recited in claim 5, wherein gas from the source of surgical gas flows through a high pressure regulator and a gas heater before the gas is delivered to the gaseous sealing manifold and the insufflation manifold.

* * * * *